United States Patent [19]

Haas et al.

[11] 4,227,013
[45] Oct. 7, 1980

[54] PROCESS FOR PREPARING POLYFUNCTIONAL COMPOUNDS

[75] Inventors: Howard C. Haas, Arlington, Mass.; Robert D. Moreau, Nashua, N.H.

[73] Assignee: Polaroid Corporation, Cambridge, Mass.

[21] Appl. No.: 35,705

[22] Filed: May 3, 1979

[51] Int. Cl.$^3$ .................... C07C 69/34; C07C 147/14; C07C 102/00

[52] U.S. Cl. ...................................... 560/190; 568/28; 260/561 R; 260/561 A; 260/561 S; 260/561 K

[58] Field of Search .................... 560/190; 260/561 R, 260/561 A, 561 S, 561 K, 607 AL

[56] References Cited

U.S. PATENT DOCUMENTS 3,560,531   2/1971   Normant .............................. 560/190

OTHER PUBLICATIONS

Tutin, J. Chem. Soc., 1907, pp. 1141–1146.
Welch, J. Chem. Soc., 1930, pp. 257–261.
Rothstein et al., J. Chem. Soc., 1953, pp. 4012–4018.
Evans, J. Chem. Soc., 1956, pp. 4691–4692.
Röhrs, C.A. 35 (1941), col. 7940 & 7941.
Matsuura, C.A. 46, col. 906 and 907.
Braeuniger et al., C.A. 65 (1966), col. 7051.

Haas et al., J. Polym. Sci., Polym Chem. Ed. 1978, 16(3), pp. 699–700.

Primary Examiner—Arthur P. Demers
Attorney, Agent, or Firm—Louis G. Xiarhos

[57] ABSTRACT

A process for preparing polyfunctional methylene-bridged compounds is disclosed. A difunctional methylene-bridged compound having acidic protons and having the formula X—CH$_2$—X is reacted with an alkali metal in the presence of a disubstituted formamide to provide a methylene-bridged polyfunctional compound having the formula

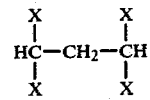

wherein X is an electron-withdrawing group such as —CONH$_2$, —COOR or —SO$_2$R where R is alkyl. The polyfunctional compounds prepared by the process of the present invention are useful in the production of metal complexing or sequestering agents, acidulents, cross-linking agents for polymeric reactions and in applications where a polyfunctional compound is desirably employed.

14 Claims, No Drawings

PROCESS FOR PREPARING POLYFUNCTIONAL COMPOUNDS

BACKGROUND OF THE INVENTION

This invention relates to a process for preparing polyfunctional compounds. More particularly, it relates to a process for preparing methylene-bridged polyfunctional compounds useful in a variety of applications where a polyfunctional compound is desirably employed.

Numerous methods have been reported in the literature for the synthesis of polyfunctional organic compounds. For example, methods for the synthesis of 1,1,3,3-tetracarboxamidopropane (TCAP) have been reported by S. Matsuura in J. Pharm. Soc. Jpn., 71, 525(1951); by W. Rohrs and S. Lang in J. Prakt. Chem., 158, 109(1941); and by H. Braeuniger and B. Stens in Pharmazie, 18, 585(1963). Similarly, a synthesis for the polyfunctional 1,1,3,3-tetrakisalkysulfonyl propanes is reported by E. Rothstein and R. Whiteley in J.Chem.-Soc.(London) 1953,4012. Frequently, methods for the organic synthesis of polyfunctional compounds require a number of steps to introduce the desired functional groups or require other laborious procedures. Oftentimes, the desired polyfunctional compound is obtained in low yield or only upon isolation or purification of one or more intermediates or by-products. Accordingly, a process whereby desired polyfunctional compounds can be simply and effectively synthesized and recovered in appreciable yield and purity will find application where the advantageous properties of polyfunctional compounds are effectively utilized.

It is an object of the present invention to provide a process for preparing methylene-bridged polyfunctional compounds.

It is another object of the present invention to provide a process for preparing such methylene-bridged polyfunctional compounds in a straightforward and effective manner.

Other objects will become apparent from the description appearing hereinafter.

SUMMARY OF THE INVENTION

These and other objects can be achieved by the present invention which resides in a process for the preparation of methylene-bridged polyfunctional compounds having the formula

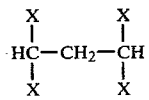

wherein each X is an electron-withdrawing group such as $-CONH_2$, $-COOR$ or $-SO_2R$ where R is alkyl. The present invention is based upon the discovery that certain organic difunctional compounds having the formula

where X is a group sufficiently electron-withdrawing to activate deprotonation of an acidic proton of the methylene bridging moiety, can be effectively reacted with an alkali metal in the presence of a disubstituted formamide, e.g., dimethyl formamide, with production of the aforesaid methylenebridged polyfunctional compound.

It has been found that such a difunctional compound, having the requisite electron-withdrawing effects of the X groups as to undergo deprotonation and formation with an alkali metal of an active carbanion salt species, can effectively undergo a nucleophilic attack upon the carbonyl carbon of a formamide. Acidification of the resulting reaction mixture provides the desired and aforesaid polyfunctional compound.

Accordingly, there is provided by the present invention a process for preparing a polyfunctional methylenebridged compound which comprises reacting a difunctonal methylene-bridged compound having the formula $X-CH_2-X$, wherein X is a group sufficiently electron-withdrawing to activate deprotonation of an acidic proton of said difunctional methylene-bridged compound, with an alkali metal in the presence of a disubstituted formamide having the formula

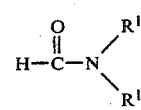

where each $R^1$ is alkyl or together both $R_1$ groups complete a heterocyclic moiety; and acidifying the resulting reaction mixture, thereby to provide a polyfunctional compound having the formula

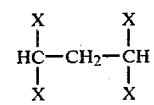

where each X group has the meaning previously ascribed.

DETAILED DESCRIPTION OF THE INVENTION

As indicated previously, the process of the present invention involves the production of a polyfunctional methylene-bridged compound having the formula

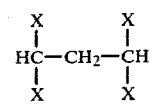

by reacting a difunctional organic compound having acidic protons and the formula $X-CH_2-X$ with an alkali metal in the presence of a disubstituted formamide, such as dimethylformamide, and acidifying the resulting reaction mixture for recovery of the desired polyfunctional compound. Thus, for example, reaction with sodium metal of a solution of malonamide dissolved in dimethylformamide produces, 1,1,3,3-tetracarboxamidopropane (TCAP). Similarly, reaction with sodium metal of a solution of diethyl malonate in dimethylformamide provides the polyfunctional compound 1,1,3,3-tetracarbethoxypropane (TCEP). A plausible, although unproven, mechanism for the reactions herein described can be set forth as follows, the reaction scheme being written as applicable to the utilization of sodium metal and dimethylformamide:

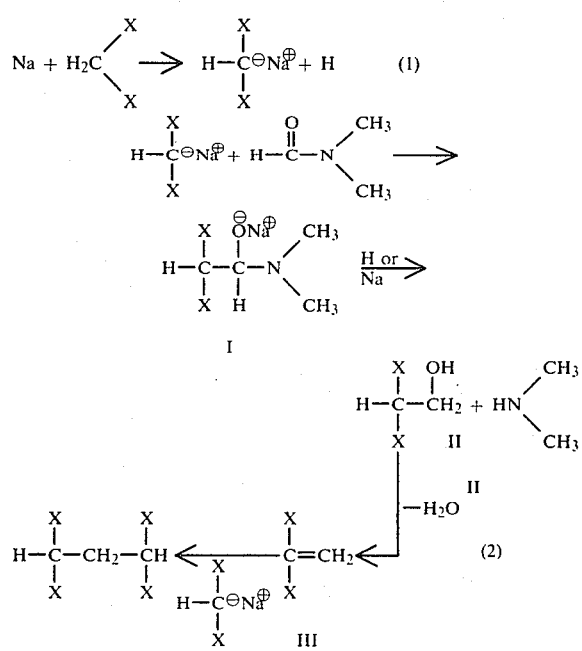

In the above reaction scheme there is, thus, shown the reaction of a difunctional organic compound having acidic protons, X—CH₂—X, and sodium metal with the formation of a carbanion salt. Nucleophilic attach of the carbonyl carbon of dimethylformamide with formation of an oxygenated intermediate (I) is shown, followed by reduction with hydrogen of sodium and formation of an hydroxymethylated species (II) with accompanying evolution of dimethylamine. Dehydration with formation of an unsaturated species (III) and Michael addition of an additional carbanion salt species is shown in the postulated mechanism as providing the desired polyfunctional compound.

Suitable difunctional organic compounds of the formula X—CH₂—X, and useful in the conduct of the process of the invention, are those having X groups sufficiently electronwithdrawing as to activate deprotonation of an acidic proton of the bridging methylene moiety and formation with an alkali metal of an active carbanion species. Examples of suitable X groups are —CONH₂, —COOR and SO₂R where R is in each instance alkyl, preferably alkyl of from 1 to 8 carbon atoms, e.g., methyl. Other X substituents, for example, trifluoromethyl or the like, can, however, be employed, provided that the X group has the requisite electron-withdrawing capacity as to permit deprotonation and formation with an alkali metal of an active carbanion species and where the X group will not readily undergo anionic attack. Similarly, the nature of electron-withdrawing group X should not be such as to result in formation of a resonance-stabilized, i.e., relatively inactive, carbanion species which will not undergo nucleophilic attach of the carbonyl carbon atom of the disubstituted formamide, e.g., dimethylformamide.

The substituent X groups of the organic difunctional reactant hereof can be the same or different. Thus, according to a preferred practice of the present invention where polyfunctional compounds having identical X groups are prepared, both X groups of the functional reactant will be the same. Examples of such compounds are malonamide, diethyl malonate and bis-methylsulfonyl methane. The substituent X groups can, however, be different and can be utilized for the production of polyfunctional compounds having mixed X groups. Suitable for the production of such compounds are difunctional reactants such as 1-carbethoxy-1-carboxamidomethane and 1-carbethoxy-1-methylsulfonyl-methane. Similarly, it will be appreciated that mixtures of difunctional reactants can be suitably employed in the conduct of the process of the invention with the production of polyfunctional compounds of varying substitution of X groups as herein defined.

The alkali metal strong bases which effect deprotonation of an acidic proton from the difunctional reactant herein described can comprise, sodium, lithium, potassium or cesium. From the standpoint of reactivity, sodium metal will be the alkali metal of choice and permits facile deprotonation in the manner described hereinbefore. Preferably, the alkali metal, e.g., sodium, will be in the form of pellets, shavings or other subdivided form in the interests of promoting reactivity. For example, sodium spheres of about ⅛ to ¼ inch in diameter have been found useful for this purpose. In the reaction scheme set forth hereinbefore, reduction of an oxygenated species (I) is shown. This reduction is believed to occur at the surface of the alkali metal and utilization of a subdivided form of sodium or like metal may be further advantageous.

The disubstituted formamide constitutes an essential reactant of the process herein described. From the reaction scheme set forth herein, it will be appreciated that the carbonyl carbon of the disubstituted formamide corresponds to that of the methylene bridging group of the polyfunctional compounds produced by the process of the invention. In addition, the disubstituted formamide serves as a solvent for the difunctional reactant, thus, facilitating the desired reaction. Suitable disubstituted formamide compounds are the dialkyl formamides, i.e., those having the formula

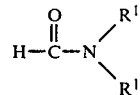

wherein each R¹ is alkyl, preferably lower alkyl of from 1 to 8 carbon atoms. The preferred formamide compound is dimethylformamide. Other useful formamides are those wherein the R¹ groups together form a heterocycle, e.g., a piperidino or morpholino group.

The amount of alkali metal employed in effecting the production of the polyfunctional compounds herein is not a critical aspect of the present invention. While some product will be formed when a small amount of base is employed relative to the methylene-bridged difunctional reactant; at least a stoichiometric molar amount of alkali metal per mole of the methylene-bridged difunctional compound should normally be employed for satisfactory yields. Amount in excess of the stoichiometric amount can be employed.

The amount of disubstituted formamide per mole of the methylene-bridged difunctional reactant can vary depending upon the particular formamide and difunctional reactants employed. In general, at least about 0.5 mole of the disubstituted formamide will be utilized per mole of the methylene-bridged difunctional compound to insure completeness of the desired reaction. Normally, the disubstituted formamide will comprise the solvent for the desired reaction and will be employed in substantial molar excess so as to provide desired reaction viscosity. It will be appreciated that the amount of disubstituted formamide will vary with the solubility of the difunctional reactant. A preferred molar ratio of disubstituted formamide to methylene-bridged difunctional reactant is from about 0.5:1 to about 20:1.

While the disubstituted formamide can be employed as a reaction solvent in the process of the present invention, the reaction mixture can comprise additional solvent or diluent materials. Since the carbanion species produced in the conduct of the process herein will react with a proton, suitable additional solvents will be aprotic solvents which under the conditions of reaction will not donate a proton to the intermediate carbanion species. Similarly, suitable additional solvents or diluents herein will be organic materials which are free of impurities which tend to react undesirably with the carbanion species. In addition, such solvent or diluent materials should be non-interfering materials which do not undergo anionic attack or otherwise interfere with the desired reaction and which are miscible with the reaction mixture. Water, for example, is desirably avoided and, accordingly, the solvents or diluents employed should be substantially anhydrous. Suitable solvent or diluent materials are to be found, for example, among aliphatic ethers such as dibutyl ether, cyclic ethers, e.g., dioxane or aromatic ethers, e.g., diphenyl ether. Hydrocarbon solvents such as benzene or like non-reactive hydrocarbons can also be employed.

The process of the present invention can be conducted over a wide range of temperatures. In general, temperatures ranging from about 15° C. to about 100° C. or higher can be suitably employed so as to assure efficient reaction rates while avoiding excessive thermal degradation of reactants. A preferred temperature range is from about 20° C. to about 50° C. In some cases, external heating of the reaction mixture will not be required due to the exothermic nature of the reaction. In some cases, cooling may be necessary or advantageous.

The desired polyfunctional compounds of the invention are obtained as the result of an acidification reaction. This is readily effected by acidifying the reaction mixture obtained as the result of the reaction of the organic methylene-bridge difunctional reactant, the disubstituted formamide and the alkali metal. The acidification neutralizes excess alkali in the reaction mixture and protonates any salt form of the desired compounds.

Any of a variety of known acids can be employed for this purpose, such as hydrochloric acid, sulfuric acid, glacial acetic acid or the like. A preferred acid is sulfuric acid which results in the formation of a by-product, sodium sulfate, readily removed from the reaction mixture by filtration or aqueous washing. The amount of acid employed is an amount sufficient to neutralize the reaction mixture. A preferred amount is a slight excess to assure complete neutralization.

The following examples illustrate the conduct of the process of the present invention. It will be understood that the specific limitations set forth in the following examples are intended as being illustrative and not limitative. All amounts and proportions, unless otherwise indicated, are by weight.

EXAMPLE I

Preparation of 1,1,3,3-tetracarboxamidopropane (TCAP)

Malonamide (10.2 g., 0.1 mole) was dissolved in 70 ml warm dimethylformamide (DMF). Sodium spheres (2.3 g, 0.1 mole), about ⅛ to ¼ in. in diam, were added, and the reaction was stirred overnight at room temperature. During this time all of the sodium disappeared. A slight excess (>0.1 mole) of glacial acetic acid was added carefully with stirring. The white solid was filtered off, washed with methanol, and dried. The yield, 7.6 g. of almost pure product, after recrystallization from $H_2O$-dimethylsulfoxide, had a melting point of 265° C. (uncorrected). The structure of TCAP was verified by infrared spectra, nuclear magnetic resonance and elemental analyses.

EXAMPLE II

Preparation of 1,1,3,3-tetracarbethoxypropane (TCEP)

Diethyl malonate (16.0 g, 0.1 mole) was dissolved in 70 ml DMF and treated with sodium spheres (2.3 g., 0.1 mole) in the manner set forth in Example I. After the reaction was complete, the reaction mixture was carefully neutralized by slowly adding 0.05 mole $H_2SO_4$ dissolved in 20 ml dioxane. Sodium sulfate was filtered off and the filtrate evaporated on a steam bath under vacuum (water aspirator) to remove dioxane and excess DMF. The viscous liquid which remained was fractionally distilled and after collecting a small amount of diethyl malonate, 5 g TCEP was collected at about 160°–165° C./1.5 mm.

The structure of TCEP was verified by infrared spectra, nuclear magnetic resonance, and elemental analyses.

EXAMPLE III

Preparation of 1,1,3,3-tetrakismethylsulfonyl propane (TMSP)

Bis-methylsulfonylmethane (4.3 g., 0.025 mole) was dissolved in 70 ml DMF and sodium spheres (0.575 g., 0.025 mole) were added in a portionwise manner. The reaction mixture was stirred overnight at room temperature. The reaction mixture was neutralized with sulfuric acid in dioxane and 20 cc. of water was added. The reaction product was filtered, washed with water, then with ethanol. The resulting product was vacuum dried at 75° C. and recrystallized from dimethyl sulfoxide. The product, TMSP, had a melting point of 278°–280° C. (uncorrected).

The structure of TMSP was verified by infrared spectra, nuclear magnetic resonance and elemental analyses.

The polyfunctional compounds prepared by the process of the present invention find utility in a number of applications where a polyfunctional compound is desirably utilized. For example, the compound 1,1,3,3-tetracarboxamidopropane (TCAP) can be hydrolyzed in known manner to effect conversion of one or more amido groups to the corresponding carboxylic acid moiety with production of a compound suited as an acidulent or complexing or sequestering agent for copper or heavy metal ions. Similarly, the compound 1,1,3,3-tetracarbethoxypropane (TCEP) can be reduced with, for example, lithium aluminum hydride, with formation of the corresponding tetra-alcohol, tetramethylol propane, suited to application as a cross-linking agent in the production of polyurethanes. It will, thus, be apparent that the present process enables the production in facile manner of a variety of polyfunctional compounds having utility in a varied technological fields.

Since certain changes can be made in many features of the above description and disclosure without departing from the spirit and scope of the invention defined in the appended claims, it is intended that all matters contained in the above description be interpreted as illustrative and not limitative.

What is claimed is:

1. A process for preparing a polyfunctional methylene-bridged compound which comprises reacting a difunctional methylene-bridged compound having the formula X—CH$_2$—X, wherein each X is selected from the group consisting of —CONH$_2$, —COOR where R is alkyl and —SO$_2$R where R is alkyl, with an alkali metal in the presence of a disubstituted formamide having the formula

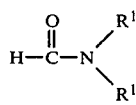

where each R$^1$ is alkyl or together both R$^1$ groups complete a heterocyclic moiety; and acidifying the resulting reaction mixture, thereby to provide a polyfunctional compound having the formula

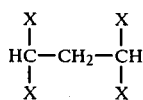

where each X group has the meaning previously ascribed.

2. The process of claim 1 wherein said difunctional methylene-bridged compound comprises malonamide.

3. The process of claim 1 wherein said difunctional methylene-bridged compound comprises diethyl malonate.

4. The process of claim 1 wherein said difunctional methylene-bridged compound comprises bis-methylsulfonylmethane.

5. The process of claim 1 wherein each R$^1$ group of said disubstituted formamide is alkyl.

6. The process of claim 5 wherein each said R$^1$ group is methyl.

7. The process of claim 1 wherein said alkali metal comprises sodium.

8. The process of claim 7 wherein said sodium is in a subdivided form.

9. The process of claim 1 wherein at least a stoichiometric molar amount of said alkali metal per mole of said methylene-bridged difunctional compound is employed.

10. The process of claim 1 wherein at least about 0.5 mole of said disubstituted formamide per mole of said methylene-bridged difunctional compound is employed.

11. The process of claim 10 wherein the molar ratio of said disubstituted formamide to said methylene-bridged difunctional compound comprises from about 0.5:1 to about 20:1.

12. The process of claim 1 wherein the process is conducted at a temperature in the range of from about 15° C. to about 100° C.

13. The process of claim 12 wherein said temperature is in the range of from about 20° C. to about 50° C.

14. The process of claim 1 wherein said acidifying reaction is effected with an amount of acid sufficient to neutralize the reaction mixture.

* * * * *